United States Patent [19]

Ridley et al.

[11] 4,058,615

[45] Nov. 15, 1977

[54] SKELETAL MUSCLE RELAXANT COMPOSITIONS COMPRISING α,α-DIPHENYL-3-TROPIDINEETHANOL AND METHODS OF PRODUCING SKELETAL MUSCLE RELAXATION

[75] Inventors: Peter Tone Ridley, Lafayette Hill; Edwin Frank Weidley, Ridley Park, both of Pa.

[73] Assignee: SmithKline Corporation, Philadelphia, Pa.

[21] Appl. No.: 727,553

[22] Filed: Sept. 28, 1976

[51] Int. Cl.² ............................................. A61K 31/46
[52] U.S. Cl. ................................................... 424/265
[58] Field of Search ...................... 424/265; 260/292

[56] References Cited

PUBLICATIONS

Zirkle et al., Journal of Med. & Pharm. Chem. 5, 341–356 (1962).

*Primary Examiner*—Stanley J. Friedman
*Attorney, Agent, or Firm*—Joseph A. Marlino; Richard D. Foggio; William H. Edgerton

[57] ABSTRACT

Pharmaceutical compositions having direct acting skeletal muscle relaxant activity comprising α,α-diphenyl-3-tropidineethanol and methods of producing skeletal muscle relaxant activity by administering internally said compositions.

2 Claims, No Drawings

SKELETAL MUSCLE RELAXANT COMPOSITIONS COMPRISING α,α-DIPHENYL-3-TROPIDINEETHANOL AND METHODS OF PRODUCING SKELETAL MUSCLE RELAXATION

This invention relates to pharmaceutical compositions which are useful for spastic disorders of skeletal muscles and to a method of producing skeletal muscle relaxant activity by administering said compositions. The compositions of this invention help relieve myopathic disorders such as, for example, myotonia, night cramps, or motor deficiencies resulting from disorders of muscle cell metabolism. More specifically, the compounds of this invention comprise α,α-diphenyl-3-tropidineethanol as the active medicament.

Most advantageously the compositions of this invention are in dosage unit form and comprise a nontoxic pharmaceutical carrier and a tropidineethanol having the following formula:

FORMULA I

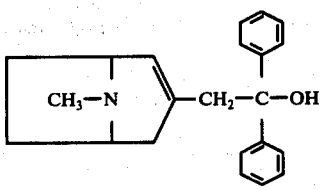

The compound of this invention has been demonstrated as having direct acting spastic skeletal muscle relaxation activity without tropane-like side effects when tested against chemically induced myotonia in mice. The skeletal muscle effects induced by the administration of anthracene-9-carboxylic acid have been reported to be markedly similar to hereditary myotonia in the goat and to myotonia congentia in humans (J. Physiol. 219, 367–383, 1971).

Briefly, the test comprises dividing mice into two groups. The first group was administered the compound of Formula I. After an appropriate pretreatment time, a 10 mg./kg. dose of anthracene-9-carboxylic acid was administered orally to both groups. The mice were then tested for hind limb spasms at frequent intervals by pinching the skin over the sacral portion of the back. This stimulation was sufficient to evoke an episode of skeletal muscle spasms in 100 percent of the control group. The percentage of mice in the treatment group that did not show spasms after pinching with forceps for a period of thirty minutes after administering the anthracene-9-carboxylic acid was calculated.

Compounds which are known to be clinically effective as direct acting skeletal muscle relaxants such as, for example, sodium dantrolene and quinine are also effective in blocking the chemically induced myotonic syndrome. The compound of this invention produced an $ED_{50}$ of 18.0 mg./kg. as compared to 6.0 mg./kg. and 33.3 mg./kg. for sodium dantrolene and quinine respectively when given orally in the above test.

The primary defect in natural and artifically induced myotonia is in the muscle itself and not on the central or peripheral nervous system. The compound of this invention acts directly on, and relaxes, spastic skeletal muscle fibers in abnormal muscle disorders and not on normal muscles. This differs from centrally acting muscle relaxants which relax normal muscle.

Despite the tropane-atropine like structure of the compound of Formula 1, it unexpectedly does not have the anticholinergic activity or the mydriatic and antisalivary side effects which are common to known potent atropine-like anticholinergic agents.

The tropidineethanol as illustrated in Formula 1 and present in these novel compositions is prepared by methods well known to the art. For example, the corresponding unsaturated ester such as ethyl-3-tropidineacetate is reacted with phenyllithium under an atmosphere of dry nitrogen. This method of preparation is disclosed in J. Org. Chem. 5, 347, 1962.

The invention also includes nontoxic pharmaceutically acceptable addition salts of the above base formed with organic and inorganic acids. Such salts are easily prepared by methods known to the art. The base is reacted with either the stoichiometric amount of organic or inorganic acid in aqueous miscible solvent, such as acetone or ethanol, with isolation of the salt by concentration and cooling or an excess of the acid in aqueous immiscible solvent, such as ethyl ether or chloroform, with the desired salt separating directly. Exemplary of such organic salts are those with maleic, fumaric, benzoic, ascorbic, pamoic, succinic, bismethylenesalicyclic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic, and theophylline acetic acids as well as with the 8-halotheophyllines for example, 8-chlorotheophylline and 8-bromotheophylline. Exemplary of such inorganic salts are those with hydrochloric, hydrobromic, sulfuric, sulfamic, phosphoric and nitric acids. These salts may also be prepared by the classical method of double decomposition of appropriate salts which is well known to the art.

The pharmaceutical compositions of this invention are prepared in conventional dosage unit forms by incorporating an amount of Formula I sufficient to provide skeletal muscle relaxant activity without the toxic effects, with a nontoxic pharmaceutical carrier according to procedures known to the art. Preferably, the composition will contain the tropidineethanol in an amount of from about 25 mg. to about 100 mg. per dosage unit.

The pharmaceutical carrier employed may be, for example, either a solid or liquid. Exemplary of solid carriers are lactose, terra laba, sucrose, talc, gelatin, agar, pectin, sugar seeds, acacia, magnesium stearate, stearic acid, and the like. Exemplary of liquid carriers are syrup, peanut oil, olive oil, water and the like. Similarly the carrier or diluent may include any time delay material well known to the art, such as, for example, glyceryl monostearate or glyceryl distearate alone or with a wax.

A wide variety of pharmaceutical forms can be employed. Thus, if a solid carrier is used the preparation can be tableted, placed in a hard gelatin capsule in powder or sustained release pellet form for in the form of a troche or lozenge. The amount of solid carrier will vary widely but preferably will be from about 25 mg. to about 1 gm. If a liquid carrier is used, the preparation will be in the form of a syrup, emulsion, soft gelatin capsule, sterile injectable liquid such as an ampule or an aqueous or nonaqueous liquid suspension.

The method in accordance with this invention comprises administering internally to animals, preferably humans, in an amount sufficient to produce skeletal muscle relaxant activity a compound as represented by Formula I combined with a pharmaceutical carrier. The tropidineethanol active ingredient will be administered in a dosage unit, preferably in in an amount of from about 25 mg. to about 100 mg. The route of administration may be parenterally or orally, the oral route being preferred. Advantageously equal doses will be administered one to four times daily with the daily dosage regimen being from 25 mg. to about 400 mg. of active ingredient.

When the method of administration described above is carried out, skeletal muscle relaxant activity is achieved without the concomitant mydriatic or antisalivary side effects common to potent tropane anticholinergic agents.

The following examples are not limiting but are illustrative of compounds of this invention and the procedures for their preparation. Other variations of this invention will be obvious to those skilled in the art.

EXAMPLE 1

Under an atmosphere of dry nitrogen, 1.5 gm. of lithium wire in 20 ml. of ether is reacted with 5.65 gm. of bromobenzene in 50 ml. of ether. A solution of 1.5 gm. of ethyl 3-tropidineacetate in 30 ml. of ether is added and mild reflux maintained throughout the addition. The reaction mixture is then stirred under reflux for about four hours, cooled and treated with saturated ammonium chloride solution and extracted several times with ether. The extracts are dried and concentrated to give an oil which is treated with citric acid in acetone-ether (1.1 mole ratio) to yield $\alpha,\alpha$-diphenyl-3-tropidineethanol citrate as white crystals having a melting point of 195°–199° C.

EXAMPLE 2

| Ingredients | Amounts |
|---|---|
| $\alpha,\alpha$-Diphenyl-3-tropidineethanol | 75.00 mg. |
| Magnesium Stearate | 2.00 mg. |
| Lactose | 130.00 mg. |

The above powders are thoroughly mixed and filled into a No. 2 hard gelatin capsule.

One capsule is administered twice a day.

EXAMPLE 3

| Ingredients | Amounts |
|---|---|
| $\alpha,\alpha$-Diphenyl-3-tropidineethanol | 25.00 mg. |
| Calcium sulfate dihydrate | 125.00 mg. |
| Sucrose | 25.00 mg. |
| Starch | 15.00 mg. |
| Talc | 5.00 mg. |
| Stearic Acid | 3.00 mg. |

The sucrose, calcium sulfate and tropidineethanol are thoroughly mixed and granulated with a hot 10% gelatin solution. The melted mass is passed through a No. 6 mesh screen directly onto drying trays. The granules are dried at 120° F. and passed through No. 20 mesh screen. These granules are then mixed with the starch, talc and stearic acid, passed through a No. 60 mesh screen and compressed into tablets.

One tablet is administered four times a day.

EXAMPLE 4

| Ingredients | Amounts |
|---|---|
| $\alpha,\alpha$-Diphenyl-3-tropidineethanol hydrochloride | 2.00 gms. |
| Sodium chloride | 0.375 gms. |
| Water for Injection | q.s. 100.00 ml. |

The salts are dissolved in part of the water and then the volume is brought up to 100 ml. The solution is filtered through a selos filter, filled into ampules and autoclaved.

EXAMPLE 5

| Ingredients | Amounts |
|---|---|
| $\alpha,\alpha$-Diphenyl-3-tropidineethanol citrate | 100.00 mg. |
| Magnesium stearate | 2.00 mg. |
| Lactose | 125.00 mg. |

The ingredients are mixed and filled into a No. 2 hard gelatin capsule.

One capsule is administered four times a day.

What is claimed is:

1. The method of producing skeletal muscle relaxant activity in abnormal muscle disorders but having no relaxant activity on normal muscle which comprises administering internally to an animal having said disorder an amount sufficient to produce said activity of a chemical compound of the formula:

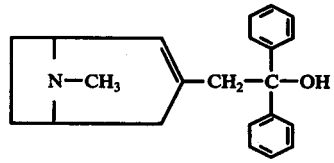

or a pharmaceutically acceptable acid addition salt of said compound.

2. The method of claim 1 in which the active medicament is administered in a daily dosage regimen of from about 25 mg. to about 400 mg.